United States Patent [19]

Bindra et al.

[11] Patent Number: 4,725,339
[45] Date of Patent: Feb. 16, 1988

[54] METHOD FOR MONITORING METAL ION CONCENTRATIONS IN PLATING BATHS

[75] Inventors: Perminder Bindra, Ossining; Solomon L. Levine, Vestal; David N. Light, Briarcliff Manor, all of N.Y.

[73] Assignee: International Business Machines Corporation, Armonk, N.Y.

[21] Appl. No.: 579,733

[22] Filed: Feb. 13, 1984

[51] Int. Cl.[4] ............................................. G01N 27/48
[52] U.S. Cl. ................................... 204/1 T; 204/434; 427/10
[58] Field of Search ....................... 204/1 T, 434, 412; 427/8, 10; 364/497, 499, 500

[56] References Cited

U.S. PATENT DOCUMENTS

| | | | |
|---|---|---|---|
| 3,925,168 | 12/1975 | Costas | 204/1 T |
| 4,055,751 | 10/1977 | Bussmann et al. | 364/500 |
| 4,132,605 | 1/1979 | Tench et al. | 204/1 T |
| 4,146,437 | 3/1979 | O'Keefe | 204/1 T |
| 4,153,521 | 5/1979 | Litvak et al. | 204/105 R |
| 4,276,323 | 6/1981 | Oka et al. | 427/8 |
| 4,324,621 | 4/1982 | Kerby | 204/1 T |
| 4,336,111 | 6/1982 | Graunke | 204/1 T |
| 4,406,248 | 9/1983 | Araki et al. | 118/690 |
| 4,406,249 | 9/1983 | Araki et al. | 118/690 |

*Primary Examiner*—G. L. Kaplan
*Attorney, Agent, or Firm*—Jeffrey S. LaBaw; Marilyn D. Smith; Jesse L. Abzug

[57] ABSTRACT

A rotating disk electrode system operates at constant speed in a solution whose metal ion concentration is held constant at multiple concentrations within a range of concentration. The current at the working electrode is recorded, while the potential at the working electrode is swept at a predetermined rate for each of the concentration values. The diffusion limiting current is determined for each of the concentration values. Then the rotating disk electrode system is operated continuously in a metal plating bath whose metal ion concentration can vary. A voltage applied to the working electrode produces a current at the electrode whose magnitude is compared to the values of the previous calibration to determine the current metal ion concentration. Alternatively, a rotating disk electrode system is operated over a range of speeds in a solution whose ion concentration is held constant over a range of concentration. Current at the working electrode is measured for a given electric potential applied to the working electrode. In this way, a calibration relationship between the current at the electrode and the range of metal ion concentrations is established which can be used with current measured in the plating bath under the same conditions as those that established the calibration curve to predict the concentration of the bath.

5 Claims, 6 Drawing Figures

METHOD FOR MONITORING METAL ION CONCENTRATIONS IN PLATING BATHS

BACKGROUND OF THE INVENTION

1. Field of the Invention

This invention relates to the field of electroanalytical chemistry, and more particularly to the field of electrolytic and electroless deposition of metal on a substrate.

2. Background of the Invention

Metal plating is of interest to the electronic industry because of the high cost of many metals, which for reasons of economy requires their use in the form of thin film plated on other less costly metals or on nonconducting substrates. The metallurgical properties of the metal deposit, however, depend on the composition of the plating baths, as well as the plating parameters. For example, the concentration of metal ions in the plating bath affects the plating rate and the plating potential. Such parameters as these tend to influence the nature and magnitude of inclusions incorporated in the deposit. Inclusions in films are known to affect metallurgical properties such as hardness, ductility, uniformity, and bondability, among others. In order to ensure consistent performance of these metal films, it is necessary to maintain the concentration of the metal ions in the plating bath within a specified range and to accurately predict the level of metal ion concentration within that range.

In the prior art, in-situ electrochemical techniques for continuously monitoring and immediately determining the concentration of metal ions in a plating bath are unknown; however, techniques involving the removal of samples from the plating bath for ex-situ analysis have been described, but these cannot be adapted to automation, are time consuming and produce results not representative of current bath conditions, which can change rapidly and unpredictably particularly in baths where high volume throughput is occurring under manufacturing conditions. This invention describes an electrochemical technique that is capable of determining metal ion concentrations continuously and currently in a plating bath and is shown to be accurate, well within the acceptable standard for manufacturing operations.

SUMMARY OF THE INVENTION

A first aspect of this method for monitoring the concentration of metal ions in a metal plating bath for depositing a metal on a substrate includes operating a rotating disk electrode system, one that includes a test electrode or working electrode rotating at constant speed in a plating solution, a counter electrode and a reference electrode. In this step of the method the rotating disc electrode system operates in a solution whose concentration of metal ions is held constant at various concentrations within a range of concentrations and, therefore, requires means for maintaining the metal ion concentration constant while certain electrical measurements are taken. Next, electrical potential at the working electrode measured with respect to the reference electrode is scanned by varying the magnitude of the potential at some predetermined rate, while maintaining the metal ion concentration constant. The current at the working electrode that results from this application of potential is measured and recorded, and paired values of the measured diffusion limiting currents and the corresponding metal ion concentrations are recorded in order to establish a calibration relationship. Then, the rotating disk electrode system is operated in the metal plating bath whose metal ion concentration is to be determined. The diffusion limiting current that results from again applying an electrical potential between the working electrode and reference electrode is measured. The measured current is referred to the previously recorded relationship between the diffusion limiting currents and the corresponding metal ion concentrations determined from the calibration solution to determine the metal ion concentration in the plating bath.

A second aspect of this method, which is particularly well adapted for use in solutions for metal deposition on a substrate where the diffusion limiting current cannot be well established, includes operating the rotating disk electrode system in a solution whose concentration of the metal ions to be deposited is held constant at various predetermined concentrations within a range of concentrations. The rotating disk electrode system includes again a test electrode, a counter electrode and a reference electrode. Next, an electrical potential is applied to the working electrode with respect to the reference electrode, while the metal ion concentration of the solution is maintained constant and the rotating disk electrode is operated at various constant speeds within an acceptable range of speeds. The current produced in the working electrode that results from the application of the potential at the working electrode associated with each of the speeds of the rotating electrode system over each of the discrete metal ion concentrations of the solution is recorded. A calibration relationship is established between paired values of the current measured in the working electrode and the corresponding speed of the rotating disk electrode for each of the electric potentials applied. From this relationship, a diffusion parameter is established for each of the metal ion concentrations at which data were taken, and the current is calculated from the relationship between the diffusion parameter and the speed of the rotating electrode system. In this way, a calibration relationship is established between the diffusion limiting current and each of the metal ion concentrations at which the current values were measured. The rotating disk electrode system is then operated in the metal plating bath, an electric potential is applied to the working electrode and current is measured at the working electrode. Upon consulting the calibration relationship, the measured current is used to establish the metal concentration in the plating bath.

BRIEF DESCRIPTION OF THE DRAWINGS

The features and advantages of the invention will be apparent from the following more particular description of the preferred embodiments of the invention illustrated in the accompanying drawings.

DESCRIPTION OF THE PREFERRED EMBODIMENT

When electric potential is applied to an electrode that is immersed in a solution containing ions of a metal to be deposited on the electrode, the potential of the electrode is the control parameter that causes the species in solution to gain an electron (reduction) or to lose an electron (oxidation). As the potential of the electrode becomes more negative versus the reference electrode, it becomes more strongly reducing; therefore, the reduction reaction taking place on the electrode can be controlled by controlling the electrode potential. The current, a measure of the electron flow, is due to electron transfer which takes place when oxidation or reduction occurs on the electrode surface.

Figure 1:
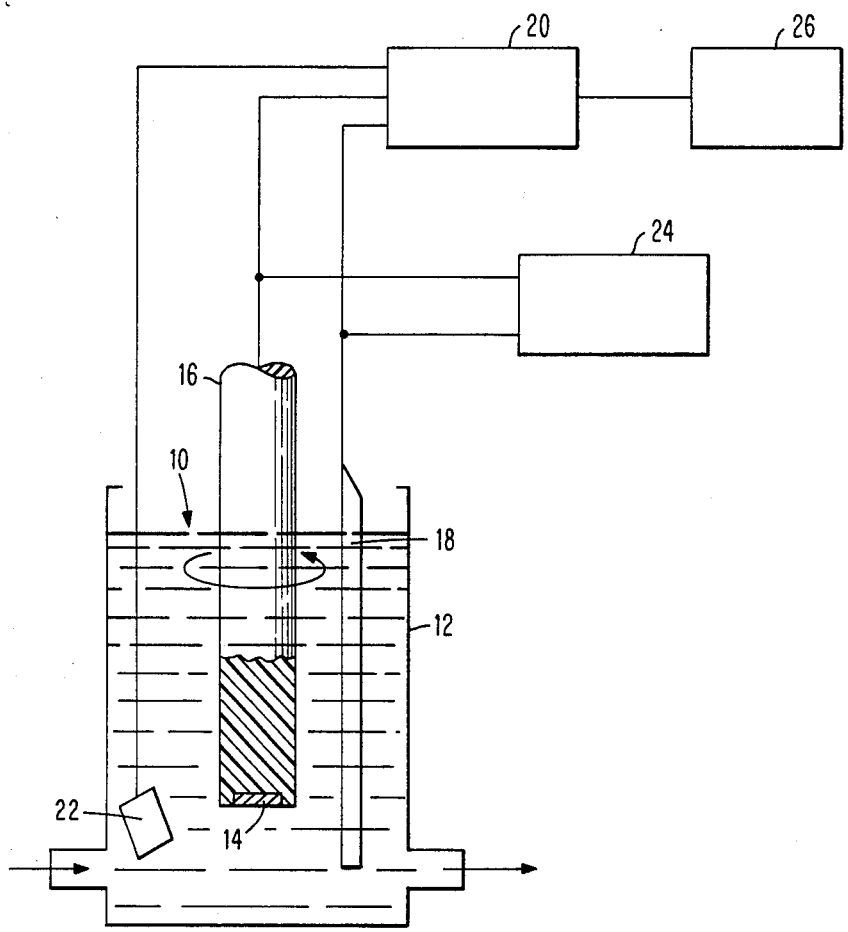
FIG. 1 is a schematic diagram of the metal ion monitoring apparatus suited for use in the practice of this invention.

Referring first to FIG. 1, a rotating disk electrode (RDE) system 10 is seen operating in a plating tank or in a flow-through side arm 12 that holds an electrolytic solution containing metal ions to be deposited on a substrate immersed in the electrolytic solution. The rotating disk electrode system includes a working electrode 14, which can be made of the same material as the substrate on which the metal ions are to be deposited, mounted at the lower end surface of a Teflon cylinder 16, which is supported for rotation in the electrolytic solution over a wide range of speed. The working electrode is the electrode where the reaction of interest occurs. A stable potential is maintained by a potentiostat 20 with respect to a reference electrode 18 also immersed in the electrolytic solution. The most common reference electrode used is saturated calomel (S.C.E.); although silver/silver chloride is sometimes employed. A counter electrode 22, made of a conductive material that is chemically inert, such as platinum, gold or graphite, is the electrode where a reaction opposite to that of the working electrode occurs. For example, when a cathodic reaction is occurring at the working electrode, an anodic reaction occurs at the counter electrode, and current flowing between the working and counter electrodes as a result of the reaction is measured. Current in the RDE system is passed between the counter electrode and working electrode, but no current passes through the reference electrode. During operation of the system, some means should be provided to remove oxygen from the solution perhaps by bubbling pure argon or another inert gas through the solution prior to taking measurements.

The potentiostat 20 applies an electric potential to the solution through the working electrode with respect to the reference electrode or S.C.E., and in this way causes an electrochemical reaction to occur. Current generated or caused by the reaction is measured or recorded by an electrometer or recorder 24. The potential at the reference electrode is stable with time and is the potential against which other potentials are compared and measured.

The potentiostat 20 controls the circuit to maintain a potential between the working and reference electrodes without drawing current through the reference electrode. A potential programmer 26 permits the circuit to vary the potential applied to the cell by the potentiostat according to some predetermined rate that varies with time or some other parameter or by way of the application of a voltage waveform. Therefore, the programmer includes a timer and may include a pulse generator. Usually incorporated in the same instrument as the potentiostat 20 is a current measuring device used to measure or monitor the current flowing between the working electrode and the counter electrode. The recorder 24 is commonly a X-Y recorder, oscilloscope or computer.

When an electrode is immersed in a solution, it attracts ion or water molecules, which, although electrically neutral, have positive and negative charges associated with opposite ends of the molecule. The electrode also attracts ions carrying an opposite charge that are held near the metal surface by forces of electrostatic attraction. In this way, an electric double layer, whose thickness is approximately 10–20 Å, is formed which has the characteristics of a condenser with a measurable capacitance. Metal ions from the solution reach by diffusion or convection the double layer where charge transformation occurs and ad-atoms diffuse on the surface of the metal electrode until they are incorporated into the metal lattice.

Figure 2:
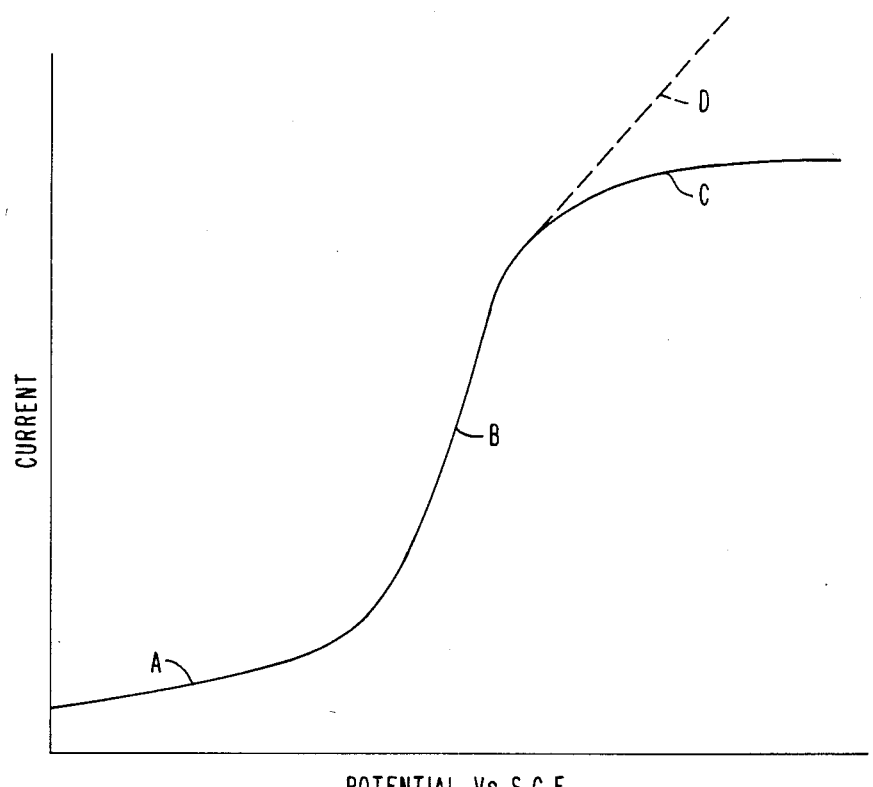
FIG. 2 is a polarization curve for the gold deposition process that shows the characteristic relationships of current at the cathode and the electrical potential at the cathode.

This process constitutes a spontaneous flow of cathodic current represented in FIG. 2 as the relationship between the potential and the current flowing. Region A of FIG. 2 is the kinetic region of the process wherein the deposition of gold is controlled by the activation energy level at which the process occurs. The effect of agitation, one of the kinetic factors, is controlled by the use of the rotating disc electrode system. While the process is occurring in the Region A, the electrical potential at the working electrode, the driving force that causes the deposition, increases and the current increases proportionally. However, when potential exceeds a first critical magnitude, the current increases rapidly and nonlinearly for incremental changes in potential. When this first critical potential is exceeded, virtually every ion at the electrode surface is reduced to an atom. When the process is operating in this region, designated zone B in FIG. 2, both kinetic and diffusion factors control the process; this region is referred to as the mixed region.

As the potential increases yet further past a second critical magnitude into the region of FIG. 2 designated zone C, the plating process is entirely controlled by diffusion effects. In this region, every ion present at the electrode is immediately converted to an atom because of the high potential applied; therefore, the arrival rate of ions at the electrode, which controls the process, is a direct function of the ion concentration in the plating solution. Hence, the rate of increase of current with increasing potential declines markedly and approaches a limiting current value at which current is constant, or nearly so, regardless of the magnitude of potential.

Convection involves the movement of substantial quantities of the solution relative to the electrode due to thermal, mechanical or other disturbances of the solution. In the model forming the basis for the principles upon which the method according to this invention is practiced, it is assumed that convection maintains the concentration of all species uniformly and equal to the bulk values up to a certain distance $\delta$ from the electrode and that, within that distance, the solution is stagnant and mass transfer occurs by way of diffusion only. The thickness of the diffusion boundary layer δ can be determined from the relationship $$\delta = 1.61\, D^{1/3} \nu^{1/6} \omega^{-1/2}$$

where D is the diffusion coefficient of the metal ions in the plating bath, $\nu$ is the kinematic viscosity and $\omega$ is the rotational speed of the RDE. The current flow i for the diffusion-controlled reaction is given by $$i = nFAD\frac{C^\infty - C^\alpha}{\delta}$$

where n is the number of electrons transferred, F is a faraday, A is the area of the working electrode of the RDE and $C^\infty$ and $C^\alpha$ are the concentrations of the metal ions in the bulk solution and at the electrode surface, respectively. Under steady state conditions, the diffusion limiting current $i_L$ becomes $$i_L = B\omega^{1/2}$$

where the diffusion parameter, $$B = 0.62\, nFD^{2/3}\nu^{-1/6} A\, C^\infty$$

These equations express a relationship between the diffusion limiting current and three quantities D, $\nu$ and C, any one of which could be determined experimentally by means of the RDE provided the other two are known.

Figure 3:
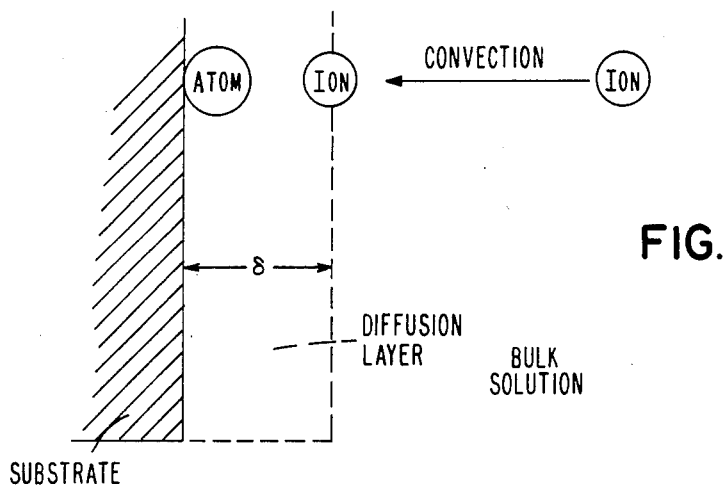
FIG. 3 is a schematic diagram illustrating the ion transport in the vicinity of the electrode and the adjacent diffusion layer.

Ions arrive at the edge of the diffusion layer by convection, as shown schematically in FIG. 3. But use of the rotating disc electrode system reduces substantially the importance of convection effects in the solution. The ions then diffuse across the diffusion layer, which is stagnant, to the electrode surface where charge transfer occurs and the ions are converted into atoms.

The method according to this invention provides a technique for monitoring continuously and automatically the concentration of metal ions in plating baths. This object is achieved by operating a rotating disk electrode system in the plating bath or in a cell in a flow-through side arm of the plating tank during the plating process. The RDE system provides known and reproducible mass transfer conditions for which the hydrodynamic equations and the convective-diffusion equation have been solved rigorously for the steady state. The mathematical treatment that forms the basis for the predictive ability of this invention is derived from the diffusion layer approach. Accordingly, it is assumed that convection maintains the concentration of all species uniform and equal to the bulk values up to the distance δ, previously defined. In solutions where the diffusion limiting current is well established and clearly defined, the method according to this invention establishes a relationship between diffusion limiting current values and the corresponding metal ion concentrations. This relationship is a calibration relationship established preferably in a solution whose concentration of metal ions can be held constant while the diffusion limiting current is determined. Then the concentration is varied over a range of concentrations so that a diffusion limiting current-ion concentration relationship is defined within the range of concentrations that will occur in the plating bath.

Figure 4:
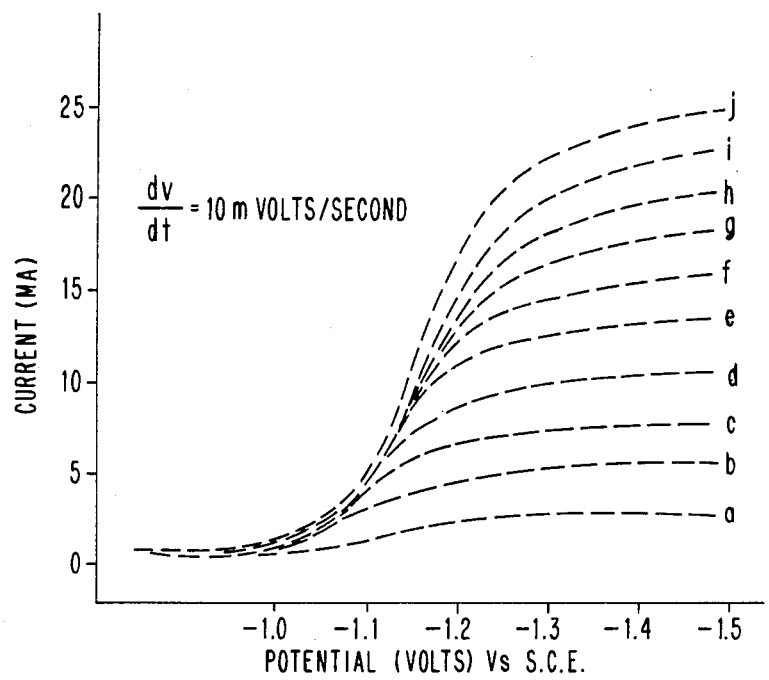
FIG. 4 is a graph that shows, over a range of metal ion concentrations in a solution, the relationship between electrode current and applied electrical potential for a particular rotational speed of a rotating disc electrode system.
Figure 5:
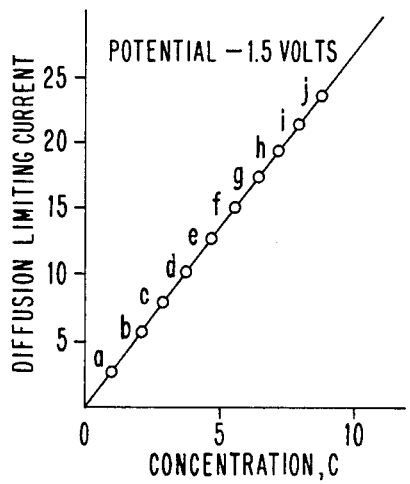
FIG. 5 is a graph that shows the relationship between diffusion limiting current and metal ion concentration.

FIG. 4 illustrates a family of curves relating current at the working electrode that results from a range of electric potential applied to the working electrode with respect to S.C.E., the reference electrode, in a plating bath where the diffusion limiting current is well defined. Notice in FIG. 4 the presence of the three zones: the kinetic region, the mixed region and the diffusion limiting region, described with reference to FIG. 2. The method that produced the data from which FIG. 4 was constructed includes operating the rotating disk electrode at a constant speed, scanning the voltage at the working electrode at the rate of approximately 10 millivolts per second, measuring the current continuously while the voltage is being scanned and repeating the voltage scan and current measurement for each of several ion concentration levels within the solution. The curves A-J correspond to each of the ion concentrations in the solution. FIG. 4 shows that when the potential at the working electrode approaches −1.5 volts, the diffusion limiting current is well defined for each of the ion concentrations. FIG. 5 shows the calibration relationship between the diffusion limiting current corresponding to −1.5 volts with respect to S.C.E. and the range of the metal ion concentrations in the solution. After the calibration curve of FIG. 5 is established, the rotating disk electrode system 10 is operated at the speed at which the calibration data were taken in a plating bath whose range of metal ion concentration can vary unpredictably. When the RDE is operating in the plating bath at the speed at which the calibration curve was constructed, an electrical potential in the limiting current region is applied to the working electrode with respect to the reference electrode and the resulting current is continuously monitored. The resulting current is used as a ordinate to enter FIG. 5; the abscissa corresponding to that ordinate is the metal ion concentration in the plating bath.

This technique has been used to predict the ion concentration of gold in a gold plating bath wherein the composition of the bath was as follows: 1-10 grams per liter of Au as $KAu(CN)_2$; $3.14 \times 10^{-2}$ molar of KCN; 1 molar KCl; and 0.1 molar of $K_2CO_3$. The pH of the plating bath was 10.8 and the temperature was 50 degrees Centigrade. Oxygen was removed from the solution by bubbling pure argon through the solution prior to taking measurements. The method according to this invention has been found to continuously indicate the concentration of gold ions in the plating bath by monitoring changes in the limiting current in the plating bath from which the concentration of the gold ions is determined.

However, when the diffusion limiting current for the deposition reaction is not well defined, for example, when the relationship between current and the potential applied to the working electrode has the shape of the region D in FIG. 2 rather than that of region C, the method according to this invention is altered somewhat to produce an accurate means for continuously predicting ion concentration in the plating bath. When the diffusion limiting current is not well defined the current at the working electrode continues to increase at a high rate as potential increases. Such a situation can occur when a secondary reaction commences before the diffusion limiting current for deposition is observed. The partial current for the secondary reaction is then superimposed on the current for the metal deposition reaction, thus making it difficult to experimentally observe the diffusion limiting current. When these conditions pertain, the current in the mixed region, i.e. region B of FIG. 2, can be used to determine the experimental value of the diffusion parameter, B. Under these conditions, the mixed control current at the working electrode (i) involved in the electron transfer reaction is controlled by both kinetic and diffusion effects and can be described by the relationship $$1/i = 1/i_k + 1/i_L = 1/i_k + 1/B\sqrt{\omega}$$

where $i_k$ is the kinetic current.

Figure 6:
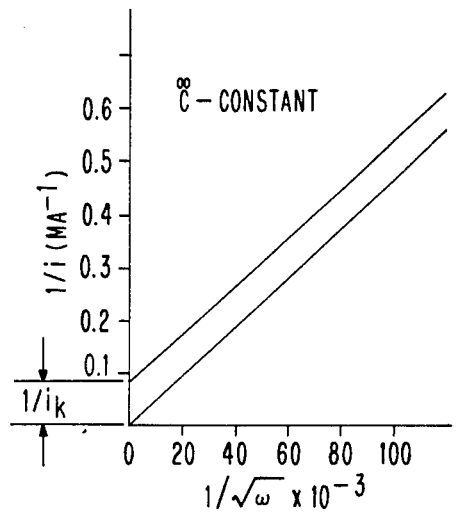
FIG. 6 is a graph that shows the relationship between current and the rotational speed of a rotating disk electrode for various levels of applied electric potential.

In this case, however, where diffusion limiting current is not well defined for a particular potential of the working electrode over a range of metal ion concentrations in a plating bath, the previously described techniques will not produce a linear relationship between current and concentration. It has been discovered, however, that the diffusion parameter, B, can be determined experimentally from the relationship between $1/i$ and $1/\sqrt{\omega}$ that results when a rotating disk electrode system is operated over a range of speeds, the current of the working electrode is measured when the RDE speed is held constant, and a known constant voltage is applied between the working electrode and the reference electrode. A typical example of the relationship thus established is shown in FIG. 6 for a constant bulk metal ion concentration and a constant applied electrical potential. If the curve established by this method does not pass through the origin, the distance from the intercept of the $1/i$ axis to the origin is a measure of the current attributable to kinetic effects, i.e., $1/i_k$. The reciprocal of the slope of the curve of FIG. 6 is equal to the magnitude of the diffusion parameter B. Further, it has been demonstrated that as the electrical potential is varied and the bulk concentration held constant, a family of curves parallel to those of FIG. 6 is defined. Moreover, as the bulk concentration is varied, the slope of the curves of FIG. 6 changes.

Changes in the value of B resulting from changes in the metal ion concentration can then be used to monitor the concentration of metal ions in the plating bath. The data used to construct the curve of FIG. 6 are recorded when the ion concentration is a constant value. Therefore, a family of curves can be established similar to that of FIG. 6 by changing the value of the concentration of metal ions in the bath while maintaining the potential of the working electrode constant. In this way, the values for the diffusion parameter for various trial values of concentration can be used to establish a calibration relationship. The magnitude of the diffusion parameter conventionally is calculated from the relationship $$B = KC$$

where K represents a constant given by $K = 0.62\, n\, F\, D^{2/3} \nu^{-1/6}$ and C is the metal ion concentration. However, according to this invention, the value of the diffusion parameter for a range of concentrations can be determined without the need to determine experimentally or to know accurately the values of the kinematic viscosity and the diffusion coefficient. It is known that experimentally determined values of the diffusion coefficient are difficult to obtain and produce widely ranging values that vary over an unacceptably large range. The breadth of this range is particularly objectionable especially when precious metals are being deposited on substrates under conditions that can change unpredictably.

After the magnitude of the diffusion parameter is established for several metal ion concentrations in the solution, the corresponding magnitude of the mixed control current can be established from the relationship $$1/i = 1/i_k + 1/B\sqrt{\omega}$$

In this way, a calibration relationship between the mixed control current and the corresponding metal ion concentration for a given potential applied to the working electrode in a plating bath wherein a rotating disk electrode is operating over a range of speed can be used to predict the metal ion concentration in the plating bath. Accordingly a calibration curve is defined similar to that of FIG. 5 except that the ordinate is the mixed control current instead of the diffusion limiting current. In order to practice the method in a solution whose diffusion limiting current is not well defined, the rotating disk electrode system is operated in the plating bath preferably at a speed that is within the speed range in which the data for the calibration relationship were established for the solution. Also the electric potential applied to the working electrode is preferably the same as the potential that was applied to develop the calibration data. When this is done, the metal ion concentration in the plating bath can be continuously monitored and accurately determined by measuring the resultant current at the working electrode of the RDE system. That measured current is the ordinate used to enter the calibration curve from which the corresponding metal ion concentration is read from the calibration curve as the actual metal ion concentration of the plating bath.

This latter technique has been used to monitor the concentration of gold ions in a gold plating bath having the following composition: 8 grams per liter of Au as $KAu(CN)_2$; 100 grams per liter of citric acid; and KOH to bring the solution to a pH of 7.6. The solution was maintained at a temperature of 23 degrees C. and the applied potential was scanned at 100 m volts per second. In a solution with such a low pH value, the diffusion limiting current is not discernible due to the onset of hydrogen evolution current. However, by employing this method, an accurate determination of the metal ion concentration in the plating bath has been made.

Although the invention has been shown and described with reference to the preferred embodiments, it will be understood by those skilled in the art that changes in composition of the plating bath and solution, the applied potential, the speed of the RDE system, the rate at which the potential is scanned and other such parameters may be made without departing from the spirit and scope of the invention.

We claim:
1. A method for monitoring the concentration of metal ions in a metal plating bath used for metal deposition on a substrate comprising:
   operating a rotating disc electrode system in a solution having a concentration of metal ions of the type to be deposited, the system including a working electrode, a counter electrode and a reference electrode;
   applying electric potential of variable magnitude between the working electrode and the reference electrode while maintaining the metal ion concen- trations of the solution constant at various concentrations within a range of said concentrations;

determining the diffusion limiting currents during metal plating at the working electrode corresponding to said various ion concentrations;

operating a rotating disc electrode system in the metal plating bath;

recording the diffusion currents that result from applying an electric potential between the working electrode and the reference electrode; and determining the metal ion concentration in the plating bath from the relationship between the metal ion concentrations and the corresponding diffusion limiting currents previously established from the solution.

2. A method for monitoring the concentration of metal ions in a metal plating bath used for metallic deposition on a substrate comprising:

operating a rotating disc electrode system in a solution having a variable concentration of metal ions of the type to be deposited, the system including a working electrode, a counter electrode and a reference electrode;

determining, for various constant metal ion concentrations in the solution, the electrical current during metal plating in working electrode that results from applying electrical potential to the working electrode with respect to the reference electrode and varying the speed of the rotating disc electrode system through a range of speed while the metal ion concentration is held constant;

determining, from the electrical currents and said speeds, the relationship between the limiting currents and the corresponding metal ion concentrations;

operating a rotating disc electrode system in the plating bath;

determining the limiting current during metal plating in the working electrode of the rotating disc electrode system that results from applying electric potential to the working electrode with respect to the reference electrode; and determining from the limiting current of the plating bath the metal ion concentration of the plating bath from the relationship between the limiting currents and the metal ion concentrations established from the solution 3. A method for monitoring the concentration of metal ions in a metal plating bath used for metallic deposition on a substrate comprising:

operating a rotating disc electrode system in a solution having a variable concentration of metal ions of the type to be deposited, the system including a working electrode, a counter electrode and a reference electrode;

determining, for various constant metal ion concentrations of the solution, the electrical current during metal plating in the working electrode that results from applying electrical potential to the working electrode with respect to the reference electrode and varying the speed of the rotating disc electrode system through a range of speed while the metal ion concentration is held constant;

determining the diffusion parameters and the kinetic currents that correspond to the various metal ion concentrations of the solution from the relationships between the electrical currents in the working electrode and the speeds of the rotating disc electrode system;

determining, from the diffusion parameters and the kinetic currents, the limiting currents that correspond to the metal ion concentrations of the solution;

operating a rotating disc electrode system in a plating bath;

determining the electrical current in the working electrode that results from applying electrical potential to the working electrode with respect to the reference electrode and varying the speed of the rotating disc electrode system through a range of speed;

determining the diffusion parameter and the kinetic current of the plating bath from the relationship between the electrical current in the working electrode and the speed of the rotating disc electrode system;

determining, from the diffusion parameter and the kinetic current, the limiting current that corresponds to the metal ion concentration of the plating bath; and determining from the limiting current of the plating bath the metal ion concentration of the plating bath from the relationship between the limiting currents and the metal ion concentrations established from the solution.

4. The method of claim 3 wherein determining the diffusion parameters that correspond to the various metal ion concentrations of the solution comprises:

establishing for the various metal ions concentrations of the solution the relationship between the electrical current in the working electrode and the corresponding speed of the rotating disc electrode system; and determining for the various metal ion concentrations of the solution the slope of the straight line that passes through the mean of the reciprocals of the electrical current in the working electrode and the corresponding speed of the rotating disc electrode system.

5. The method of claim 4 wherein determining the limiting currents i that correspond to the various metal ion concentrations of the solution comprises:

determining the magnitude of the kinetic current i as the intercept of the reciprocal of the electrical current axis by said straight line; and calculating the limiting current i from the relationship $$1/i = 1/i_k + 1/B\sqrt{\omega}$$

where B is the diffusion parameter of the solution and $\omega$ is the speed of the rotating disc electrode system.

* * * * *